United States Patent
Zhu et al.

(10) Patent No.: US 11,680,134 B2
(45) Date of Patent: Jun. 20, 2023

(54) METHOD FOR SYNTHESIZING POLYOLEFIN MATERIAL WITH CONTROLLED DEGREE OF BRANCHING

(71) Applicant: SHANGHAI JIAO TONG UNIVERSITY, Shanghai (CN)

(72) Inventors: Xinyuan Zhu, Shanghai (CN); Ning Ren, Shanghai (CN); Gangsheng Tong, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 399 days.

(21) Appl. No.: 16/978,780

(22) PCT Filed: Nov. 15, 2018

(86) PCT No.: PCT/CN2018/115550
§ 371 (c)(1),
(2) Date: Sep. 8, 2020

(87) PCT Pub. No.: WO2020/015260
PCT Pub. Date: Jan. 23, 2020

(65) Prior Publication Data
US 2021/0047462 A1     Feb. 18, 2021

(30) Foreign Application Priority Data
Jul. 20, 2018   (CN) .......................... 201810805821.0

(51) Int. Cl.
*C08G 61/08* (2006.01)
*C07C 13/263* (2006.01)

(52) U.S. Cl.
CPC ............ *C08G 61/08* (2013.01); *C07C 13/263* (2013.01); *C07C 2601/18* (2017.05);
(Continued)

(58) Field of Classification Search
USPC .......................................................... 526/308
See application file for complete search history.

(56) References Cited

U.S. PATENT DOCUMENTS

| | | | | |
|---|---|---|---|---|
| 3,306,948 A | * | 2/1967 | Kealy | ...................... B01J 31/20 |
| | | | | 976/DIG. 45 |
| 2012/0225290 A1 | * | 9/2012 | Hartmann | ............. C08F 136/06 |
| | | | | 525/332.8 |
| 2013/0164548 A1 | * | 6/2013 | Tasaka | ..................... C09D 7/65 |
| | | | | 524/106 |

FOREIGN PATENT DOCUMENTS

| CN | 101312650 A | 11/2008 |
|---|---|---|
| CN | 102906202 A | 1/2013 |

(Continued)

OTHER PUBLICATIONS

Miller et al, Codimerization of alpha-Olefins and Conjugated Dienes by a Nickel-Based Coordination Catalyst, Journal of the American Chemical Society, 89(15), 3756-3761, 1967. (Year: 1967).*
(Continued)

*Primary Examiner* — Fred M Teskin
(74) *Attorney, Agent, or Firm* — Bayramoglu Law Offices LLC

(57) ABSTRACT

A method for synthesizing polyolefin materials with a controlled degree of branching includes the following steps: polymerizing cyclic olefin monomers under catalyst conditions. The cyclic olefin monomer is shown in formula I, where n≥0, n is an integer. By changing monomers and reaction parameters such as reaction temperature, solvent type, catalyst concentration, monomer concentration and reaction time, the degree of branching, the molecular weight and molecular weight distribution of polyolefin can be controlled. Compared with the existing process, the present invention is a new polymerization process, which can prepare the hyperbranched polyolefin with precise and controllable branching structure. The polyolefin material prepared according to the present invention has advantages of a controlled degree of branching, low viscosity and good (Continued)

fluidity, which has broad application in coating, lubricant, polymer and process flow improvement technologies.

7 Claims, 3 Drawing Sheets

(52) U.S. Cl.
CPC .... *C08G 2261/11* (2013.01); *C08G 2261/132* (2013.01); *C08G 2261/3323* (2013.01); *C08G 2261/3327* (2013.01)

(56) References Cited

FOREIGN PATENT DOCUMENTS

| CN | 102985497 A | 3/2013 |
|---|---|---|
| CN | 103038299 A | 4/2013 |
| EP | 2585514 A1 | 5/2013 |
| WO | 2012121848 A2 | 9/2012 |
| WO | 2017194654 A1 | 11/2017 |

OTHER PUBLICATIONS

Guan, et al, "Chain Walking: A New Strategy to Control Polymer Topology", SCIENCE, vol. 283, Mar. 26, 1999, p. 2059-2062.

Bogdanovic, Borislav, et al, "A Catalyzed Asymmetric Synthesis", Angew. Chem. internat. Edit., vol. 11, No. 11, Dec. 31, 1972, p. 1023-1024.

Shi et al, "Synthesis of amphiphilic poly(cyclooctene)-graft-poly(ethylene glycol) copolymers via ROMP and its surface properties", Polym. Chem., Dec. 14, 2010, p. 679-684.

Li et al, "Study on changes of volatile components in instant scallop before and after sterilization", Science and Technology of Food Industry, vol. 33, No. 4, Feb. 15, 2012, p. 117-121.

\* cited by examiner

METHOD FOR SYNTHESIZING POLYOLEFIN MATERIAL WITH CONTROLLED DEGREE OF BRANCHING

CROSS REFERENCE TO THE RELATED APPLICATIONS

This application is the national phase entry of International Application No. PCT/CN2018/115550, filed on Nov. 15, 2018, which is based upon and claims priority to Chinese Patent Application No. 201810805821.0, filed on Jul. 20, 2018, the entire contents of which are incorporated herein by reference.

TECHNICAL FIELD

The present invention relates to the technical field of polyolefin, and in particular, to a method for synthesizing polyolefin material with a controlled degree of branching.

BACKGROUND

Polyolefin is a kind of polymer material that has a longest history, the highest yield and the broadest application. Polyolefin has the simplest composition, which is only composed of carbon and hydrogen elements. Although the composition is simple, polyolefin materials possess a variety of properties because their chemical structure may change. Common polyolefin materials include polyethylene, polypropylene, polybutadiene, poly-α-olefin, and others, which play an irreplaceable role in various fields of daily life and industrial production. Polyolefin materials exhibit different properties with the change of their chemical structure, molecular weight, molecular weight distribution, fillers and processing methods. The chemical structure of the polyolefin is the primary factor that determines its corresponding physical properties. This kind of material is usually only composed of carbon and hydrogen elements, the chain structure thereof, however, could vary greatly. Polyolefin materials have different branched chain structures, and length, density and arrangement of these branched chains will have a profound impact on the properties of materials. For example, polyethylene materials, according to the degree of branching and molecular weight, can be divided into ultra-high molecular weight polyethylene (UHMWPE), high-density polyethylene (HDPE), linear low-density polyethylene (LLDPE), low-density polyethylene (LDPE). Normally, the higher the degree of branching in polyolefin materials, the lower the crystallinity of the materials, which results in reduced viscosity, better fluidity, and higher processability. Polyolefin materials have application in coating, lubricant, crosslinking agents and other fields.

Due to the limitation of current synthetic methods, the synthesis of polyolefins with a high degree of branching is challenging. Although Guan Zhibin et al. proposes the method of "chain walking polymerization" in the 1990's to synthesize polyolefin materials with a high degree of branching (Science, Vol 283, 1999), this method is limited by the reaction mechanism and the catalyst, so it is difficult to control the branched structure of resulting polymers. The branching length of polyolefin materials obtained by this method presents random distribution due to the restriction of statistical laws, thus affecting the properties of materials. Therefore, it is highly desirable to provide a new method for synthesizing polyolefin material that is controllable and yields precise branching structure.

SUMMARY

The technical problem to be solved by the present invention is, in view of the deficiencies existing in the prior art, to provide a method for synthesizing polyolefin materials with a controlled degree of branching. Specifically, disclosed is a method of precise and controllable hyperbranched polyolefin synthesis. The degree of branching, molecular weight and molecular weight distribution of polyolefin can be controlled by regulating various parameters during reaction. As a result, the synthesis of hyperbranched polyolefin with precise and controllable branched structure that is otherwise unobtainable can be achieved.

The object of the present invention is accomplished by the following technical solutions.

The present invention provides a method for synthesizing polyolefin materials with a controlled degree of branching, including the following steps:

polymerizing cyclic olefin monomer under catalyst conditions;

wherein the cyclic olefin monomer is shown in formula I:

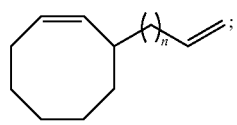

formula I where n≥0, n is an integer.

Preferably, in the polymerization reaction, the molar concentration of the cyclic olefin monomer is 0.2-2 mol/L, more preferably 0.2-1 mol/L. When the concentration of the monomer in the reaction exceeds 1 mol/L, the reaction will be uncontrolled due to cross-linking caused by excessively high degree of branching, resulting in that the obtained polymer is insoluble in an organic solvent; when the concentration of the monomer is less than 1 mol/L, linear or branched polymers can be formed.

Preferably, the catalyst is selected from organometallic catalyst.

Preferably, the organometallic catalyst is at least one selected from the group consisting of ruthenium-containing organometallic catalyst, molybdenum-containing organometallic catalyst and tungsten-containing organometallic catalyst. The catalyst for the present invention has an excellent olefin metathesis catalytic ability.

Preferably, a concentration ratio of the cyclic olefin monomer to the catalyst is 200-4000:1. When the ratio of the monomer to the catalyst is 1000:1 or higher, the reaction rate is slow, the degree of branching is low, the molecular weight is high and the molecular weight distribution is narrow. When the ratio of the monomer to the catalyst is 500:1 or lower, the reaction rate is faster, the degree of branching is higher, the molecular weight is lower and the molecular weight distribution is broader.

Preferably, a polymerization reaction temperature is 0-50° C., and a reaction time is 0.5-72 h. As the reaction temperature increases, the degree of branching during the reaction increases. For example, when the reaction temperature is 50° C., the degree of branching in the polymer obtained can reach 30.7%, yielding a hyperbranched structure. When the reaction temperature is 27° C., the degree of branching in the polymer obtained is only 5.3%, showing a linear structure.

More preferably, when the target polymer has the hyperbranched structure, the polymerization reaction temperature is controlled at 50° C. and the reaction time is 72 h. When the target polymer has the linear structure, the polymerization reaction temperature is controlled at 0° C. and the reaction time is 3 h.

Preferably, the polymerization reaction is carried out in the presence of the organic solvent including at least one selected from the group consisting of tetrahydrofuran, acetone, toluene, chloroform and dichloromethane.

The present invention also provides a cyclic olefin monomer, and the cyclic olefin monomer is shown in formula I:

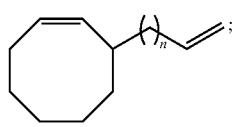

formula I where n≥0, n is an integer.

The present invention also provides an application of the cyclic olefin monomer in the synthesis of polyolefin materials with a controlled degree of branching.

The number of two adjacent tertiary carbon atoms in the product obtained by the method of the present invention is determined by the number of carbon atoms between two unsaturated carbon functional groups participating in the metathesis reaction in monomer. When the reaction temperature increases, the degree of branching in the product increases, and vice versa. When the reaction concentration increases, the molecular weight of the product increases, and the molecular weight distribution becomes broader, and vice versa. When the concentration of the monomer increases, the degree of branching and the molecular weight increase, and vice versa. When the catalyst content increases, the molecular weight of the product increases, the molecular weight distribution becomes broader, the degree of branching increases, and vice versa. When the reaction time increases, the molecular weight of the product increases, the molecular weight distribution becomes broader, and the degree of branching in the product increases.

Compared with the prior art, the present invention has the following advantages:

The present invention specially designs a series of cyclic olefin monomers and performs polymerization reaction on these monomers to form polymers. By changing monomers and reaction parameters such as reaction temperature, solvent type, catalyst concentration, monomer concentration and reaction time, the degree of branching, the molecular weight and the molecular weight distribution of polyolefin can be controlled. Thus the hyperbranched polyolefin with precise and controllable branched structure can be prepared.

The polyolefin material prepared according to the present invention has advantages of a controlled degree of branching, low viscosity and good fluidity, and can be widely used in the fields of coatings, lubricants, polymer processing flow improvers and others.

BRIEF DESCRIPTION OF THE DRAWINGS

Other features, objectives and advantages of the present invention will become more obvious by reading the detailed description of the non-restrictive embodiments with reference to the following drawings.

DETAILED DESCRIPTION OF THE EMBODIMENTS

The present invention is described in detail below in combination with specific embodiments. The following embodiments will help those skilled in the art to further understand the present invention, but will not limit the present invention in any form. It should be pointed out that for ordinary technical personnel in the art, several changes and improvements can be made without departing from the concept of the present invention. These belong to the protection scope of the present invention.

Embodiment 1

Figure 1:
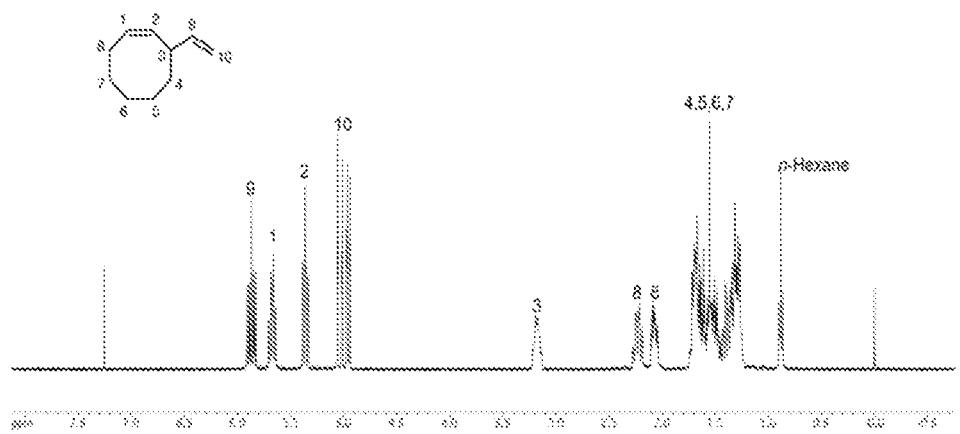
FIG. 1 is a diagram showing a structure and a $^1$H nuclear magnetic resonance (NMR) spectrum of 3-vinyl-1-cyclooctene synthesized in embodiment 1.

Monomer synthesis: 10 g of 3-bromocyclooctene is added into 30 ml of anhydrous tetrahydrofuran, stirred slowly under the protection of argon, and 0.1 g of cuprous iodide is added. Then, 1 mol/L vinyl magnesium bromide tetrahydrofuran solution is slowly dropped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ia, and the yield is about 40%. The 1H NMR spectrum is shown in FIG. 1.

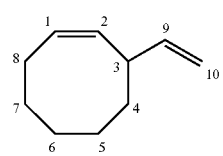

formula Ia

Polymerization reaction: 91 mg of pure monomer obtained in the above steps is added into anhydrous tetrahydrofuran to a constant volume of 880 μL (0.75 mol/L), and stirred slowly at 50° C. (stirring rate is 100 rpm), and then the solution of Grubbs 2nd Generation catalyst (2.7 mg of catalyst is dissolved in 25 μL of tetrahydrofuran, 3.7 mmol/L) is added into the reaction, and the reaction is sealed and performed for 48 h. Then 500 μL of vinyl ether is added to terminate the reaction, and methanol is used for precipitation for three times to obtain the pure polymer.

Figure 4:
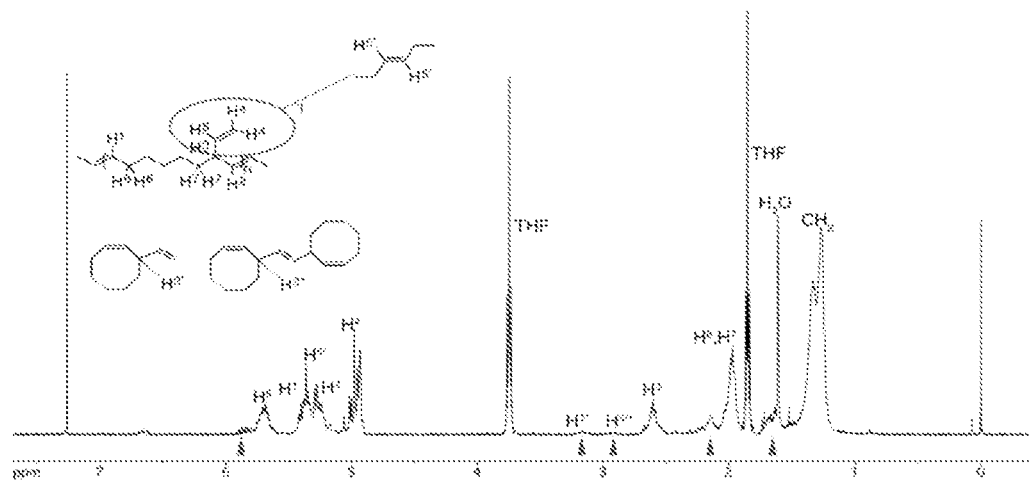
FIG. 4 is a diagram showing a branched structure and a $^1$H NMR spectrum of the product obtained from the polymerization of monomer in embodiment 1, wherein the integral value of each peak will change with the varying reaction conditions.

As shown in FIG. 4, the number average molecular weight is 0.89 kDa, the weight average molecular weight is 3.92 kDa, the molecular weight distribution is 4.4, and the degree of branching is 9.1%.

Embodiment 2

Figure 2:
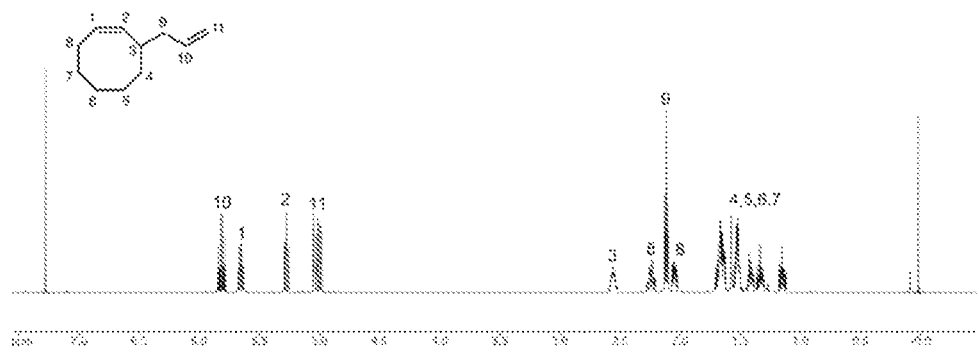
FIG. 2 is a diagram showing a structure and a $^1$H NMR spectrum of 3-allyl-1-cyclooctene synthesized in embodiments 2 to 5.

Monomer synthesis: 10 g of 3-bromocyclooctene is added into 30 ml of anhydrous tetrahydrofuran, stirred slowly under the protection of argon, and 0.1 g of cuprous iodide is added. Then, 1 mol/L allyl magnesium bromide tetrahydrofuran solution is slowly dropped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ib and the yield is about 37%. The 1H NMR spectrum is shown in FIG. 2.

formula Ib

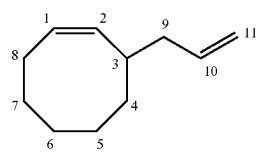

Figure 5:
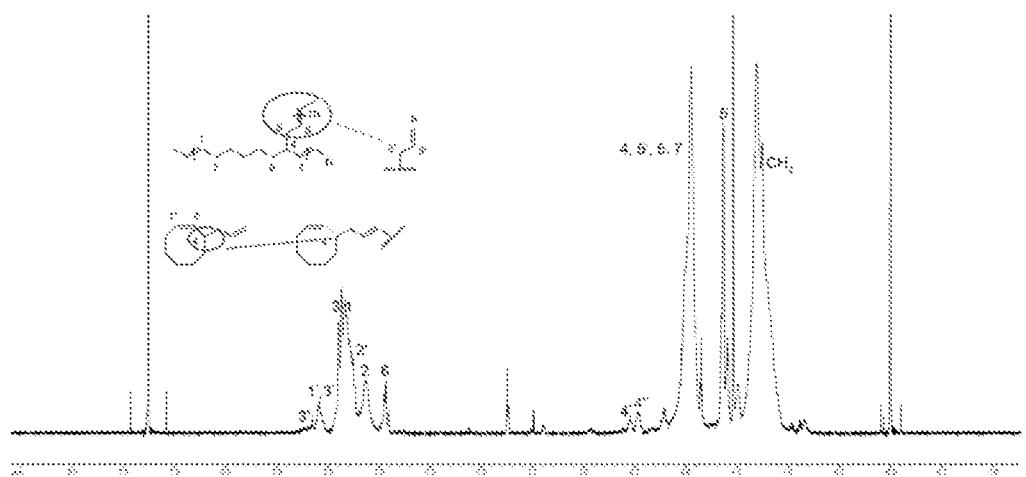
FIG. 5 is a diagram showing a branched structure and a $^1$H NMR spectrum of the products obtained from the polymerization of monomers in embodiments 2 to 5, wherein the integral value of each peak will vary with the reaction conditions (embodiments)
Figure 7:
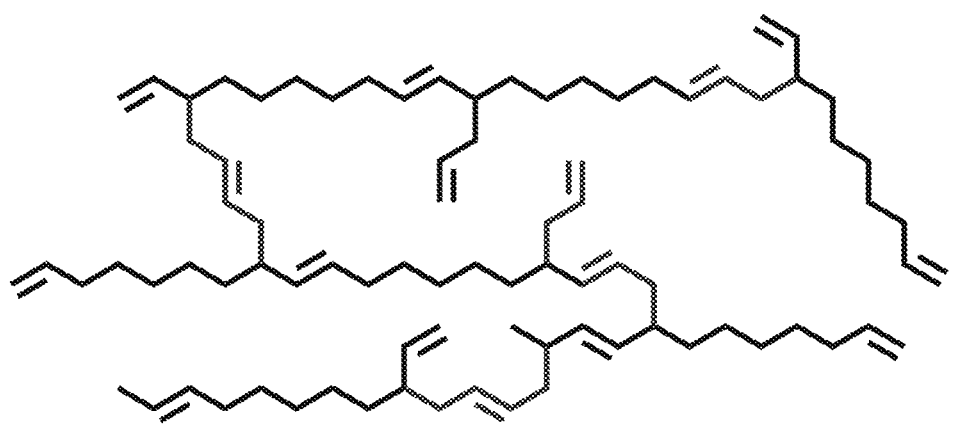
FIG. 7 is a diagram showing a branched structure of the polymer synthesized in embodiment 1.

Polymerization reaction: 100 mg of pure monomer obtained in the above steps is added into anhydrous tetrahydrofuran to a constant volume of 880 μL (0.75 mol/L), and stirred slowly at 50° C. (stirring rate is 100 rpm), and then the solution of Grubbs 2nd Generation catalyst (2.7 mg of catalyst is dissolved in 25 μL of tetrahydrofuran, 3.7 mmol/L) is added into the reaction, and the reaction is sealed and performed for 24 h. Then 500 μL of vinyl ether is added to terminate the reaction, and methanol is used for precipitation for three times to obtain the pure polymer. The branched structure of the polymer is similar to that shown in FIG. 7. The main chain structure and terminal unit are shown in FIG. 5. The number average molecular weight is 14.4 kDa, the weight average molecular weight is 86.2 kDa, the molecular weight distribution is 6.0, and the degree of branching is 30.7%. The branched structure of the polymer is shown in FIG. 7.

Embodiment 3

Monomer synthesis: 10 g of 3-bromocyclooctene is added into 30 ml of anhydrous tetrahydrofuran, and 0.1 g of cuprous iodide is added under the protection of argon, and then 1 mol/L vinyl magnesium bromide tetrahydrofuran solution is slowly dropped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ib, and the yield is about 40%.

formula Ib

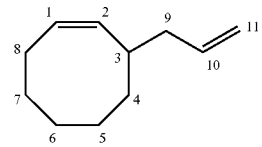

Polymerization reaction: 100 mg of pure monomer obtained in the above steps is added into anhydrous tetrahydrofuran to a constant volume of 330 μL (1 mol/L), and stirred slowly at 27° C. (stirring rate is 100 rpm), and then the solution of Grubbs 2nd Generation catalyst (2.7 mg of catalyst is dissolved in 25 μL of tetrahydrofuran, 3.7 mmol/L) is added into the reaction, and the reaction is sealed and performed for 24 h. Then 500 μL of vinyl ether is added to terminate the reaction, and methanol is used for precipitation for three times to obtain the pure polymer. The branched structure of the polymer is similar to that in FIG. 7. The main chain structure and terminal unit are shown in FIG. 5. The number average molecular weight is 38.1 kDa, the weight average molecular weight is 131.5 kDa, the molecular weight distribution is 3.4, and the degree of branching is 15.4%.

Embodiment 4

Monomer synthesis: 10 g of 3-bromocyclooctene is added into 30 ml of anhydrous tetrahydrofuran, stirred slowly under the protection of argon, and 0.1 g of cuprous iodide is added. Then, 1 mol/L vinyl magnesium bromide tetrahydrofuran solution is slowly dropped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ib, and the yield is about 40%.

formula Ib

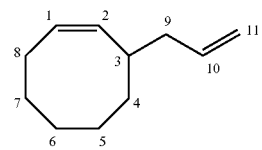

Polymerization reaction: 100 mg of pure monomer obtained in the above steps is added into anhydrous tetrahydrofuran to a constant volume of 880 μL (0.75 mol/L), and stirred slowly at 50° C. (stirring rate is 100 rpm), and then the solution of Grubbs 2nd Generation catalyst (0.135 mg of catalyst is dissolved in 25 μL of tetrahydrofuran, 0.18 mmol/L) is added into the reaction, and the reaction is sealed and performed for 24 h. Then, 500 μL of vinyl ether is added to terminate the reaction, and methanol is used for precipitation for three times to obtain the pure polymer. The branched structure of the polymer is similar to that in FIG. 7. The main chain structure and terminal unit are shown in FIG. 5. The number average molecular weight is 2.6 kDa, the weight average molecular weight is 4.8 kDa, the molecular weight distribution is 1.8, and the degree of branching is 15.4%.

Embodiment 5

Monomer synthesis: 10 g of 3-bromocyclooctene is added into 30 ml of anhydrous tetrahydrofuran, stirred slowly under the protection of argon, and 0.1 g of cuprous iodide is added. Then, 1 mol/L vinyl magnesium bromide tetrahydrofuran solution is slowly dropped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ib, and the yield is about 40%.

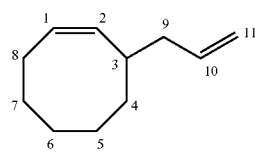

(formula Ib)

Polymerization reaction: 100 mg of pure monomer obtained in the above steps is added into anhydrous tetrahydrofuran to a constant volume of 880 μL (0.75 mol/L), and stirred slowly at 50° C. (stirring rate is 100 rpm), and then the solution of Grubbs 2nd Generation catalyst (2.7 mg of catalyst is dissolved in 25 μL of tetrahydrofuran, 3.7 mmol/L) is added into the reaction, and the reaction is sealed and performed for 6 h. Then 500 μL of vinyl ether is added to terminate the reaction, and methanol is used for precipitation for three times to obtain the pure polymer. The branched structure of the polymer is similar to that in FIG. 7. The main chain structure and terminal unit are shown in FIG. 5. The number average molecular weight is 6.5 kDa, the weight average molecular weight is 22.2 kDa, the molecular weight distribution is 3.4, and the degree of branching is 27.5%.

Embodiment 6

Monomer synthesis: 3 g of magnesium powder is added into 30 ml of anhydrous tetrahydrofuran, 8-bromo-1-octene solution (12 g dissolved in 30 ml of anhydrous tetrahydrofuran) is added under the protection of argon. After Grignard reaction begins, the reaction is maintained at room temperature for 30 min, and then heated to 50° C. for 1 hour to obtain Grignard reagent.

Figure 3:
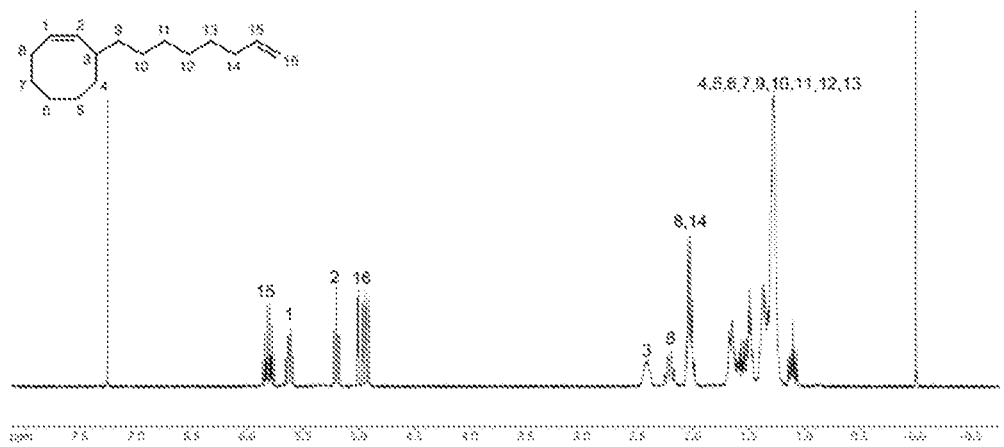
FIG. 3 is a diagram showing a structure and a $^1$H NMR spectrum of a cyclooctene derivative with 8 carbon atoms in the side group synthesized in embodiment 6.

10 g of 3-bromocyclooctene is added into 30 ml of anhydrous tetrahydrofuran, stirred slowly under the protection of argon, and 0.1 g of cuprous iodide is added. Then the Grignard reagent prepared in the present embodiment is slowly dripped at 0° C. and the reaction is performed for 3 hours. Saturated ammonium chloride solution is slowly added to the reaction solution to terminate the reaction. The reaction solution is extracted with ether for three times. The organic phase is collected and dried with saturated salt water and dried with anhydrous magnesium sulfate. Then the reaction solution is concentrated by rotary evaporation. The crude product is purified by silica gel column (the mobile phase is n-hexane) to obtain purified product. The structure of the purified product is shown in formula Ic, and the yield is about 49%. The 1H NMR spectrum is shown in FIG. 3.

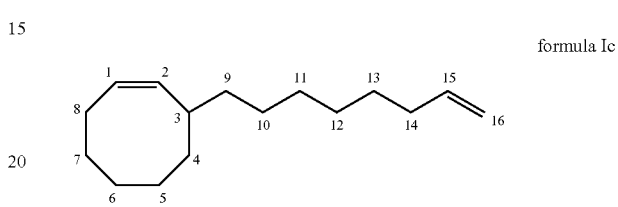

formula Ic

Figure 6:
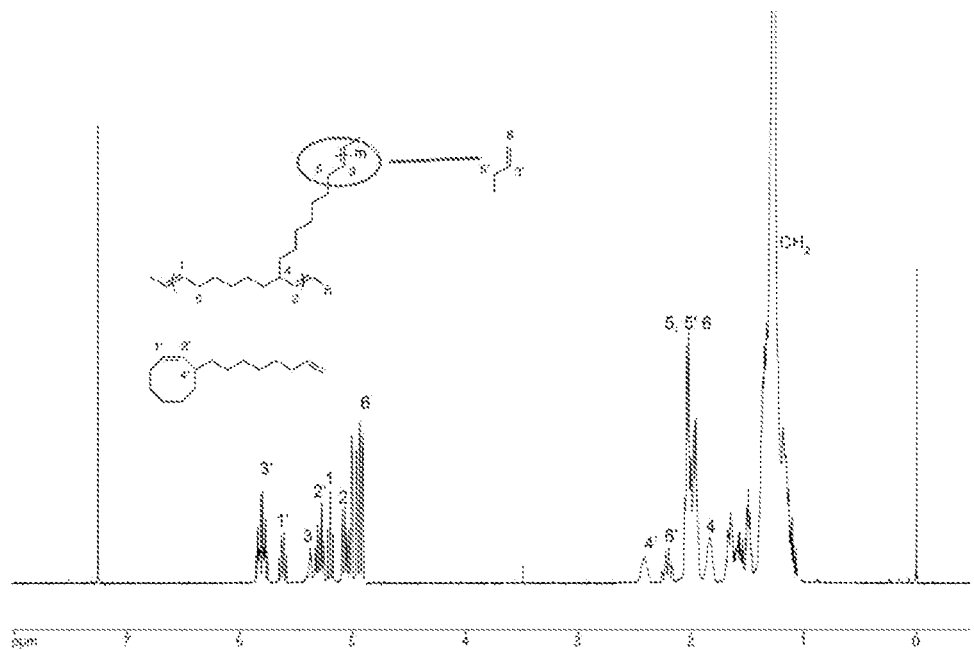
FIG. 6 is a diagram showing a branched structure and a $^1$H NMR spectrum of the product obtained from the polymerization of the monomer synthesized in embodiment 6, wherein the integral value of each peak will change with the reaction conditions.

Polymerization reaction: 147 mg of pure monomer obtained in the above steps is added into anhydrous tetrahydrofuran to a constant volume of 880 μL (0.75 mol/L), and stirred slowly at 50° C. (stirring rate is 100 rpm), and then the solution of Grubbs 2nd Generation catalyst (2.7 mg of catalyst is dissolved in 25 μL of tetrahydrofuran, 3.7 mmol/L) is added into the reaction, and the reaction is sealed and performed for 24 h. Then 500 μL of vinyl ether is added to terminate the reaction, and methanol is used for precipitation for three times to obtain the pure polymer. The branched structure of the polymer is similar to that in FIG. 7. The main chain structure and terminal unit are shown in FIG. 6. The number average molecular weight is 102 kDa, the weight average molecular weight is 534 kDa, the molecular weight distribution is 5.23, and the degree of branching is 15.6%.

It should be noted that, as an alternative to the above embodiment, when n is other values greater than or equal to 1, the structure with a controlled degree of branching shown in FIG. 7 can also be prepared.

The specific embodiment of the present invention is described above. It should be understood that the present invention is not limited to the above-mentioned specific embodiments, and those skilled in the art can make various changes or modifications within the scope of the claims, which does not affect the substantive content of the present invention. Without conflict, the embodiment of the present application and the features in the embodiment can be arbitrarily combined with each other.

What is claimed is:

1. A synthetic method for synthesizing polyolefin materials with a controlled degree of branching, comprising the following steps:
   performing a polymerization reaction on a cyclic olefin monomer under a condition of a catalyst;
   wherein the cyclic olefin monomer is shown in formula I:

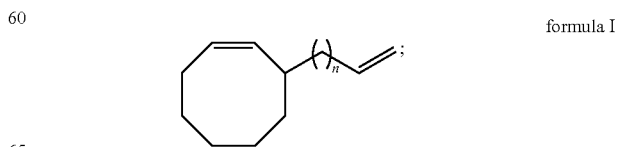

formula I where n≥0, n is an integer.

2. The synthesis method for synthesizing the polyolefin materials with the controlled degree of branching according to claim 1, wherein in the polymerization reaction, a molar concentration of the cyclic olefin monomer is 0.2-2 mol/L.

3. The synthesis method for synthesizing the polyolefin materials with the controlled degree of branching according to claim 1, wherein the catalyst is selected from a organometallic catalyst.

4. The synthesis method for synthesizing the polyolefin materials with the controlled degree of branching according to claim 3, wherein the organometallic catalyst is at least one selected from the group consisting of a ruthenium-containing organometallic catalyst, a molybdenum-containing organometallic catalyst and a tungsten-containing organometallic catalyst.

5. The synthesis method for synthesizing the polyolefin materials with the controlled degree of branching according to claim 1, wherein a molar concentration ratio of the cyclic olefin monomer to the catalyst is 200-4000:1.

6. The synthesis method for synthesizing the polyolefin materials with the controlled degree of branching according to claim 1, wherein a polymerization reaction temperature is 20-50° C., and a reaction time is 0.5-72 h.

7. The synthesis method for synthesizing the polyolefin materials with the controlled degree of branching according to claim 1, wherein the polymerization reaction is carried out in a presence of an organic solvent, and the organic solvent is at least one selected from the group consisting of tetrahydrofuran, and acetone.

* * * * *